United States Patent [19]
Laudadio

[11] Patent Number: 4,653,507
[45] Date of Patent: Mar. 31, 1987

[54] DIFFERENTIAL THERMAL TESTING APPARATUS AND METHOD

[75] Inventor: Charles Laudadio, Groton, Conn.

[73] Assignee: Pfizer Inc., New York, N.Y.

[21] Appl. No.: 537,895

[22] Filed: Sep. 30, 1983

[51] Int. Cl.$^4$ ..................... A61B 19/00; G01N 25/00
[52] U.S. Cl. ......................................... 128/742; 374/45
[58] Field of Search ...................... 374/10, 11, 13, 43, 374/44, 33, 45, 29, 34, 31, 30, 32, 15, 12; 128/736, 399, 742

[56] References Cited

U.S. PATENT DOCUMENTS

| | | | |
|---|---|---|---|
| 2,728,337 | 12/1955 | Guillemin | 128/742 |
| 2,982,132 | 5/1961 | Mendlowitz | 374/33 |
| 3,075,377 | 1/1963 | Land | 374/44 |
| 3,217,538 | 11/1965 | Loeb | 374/29 |
| 3,533,397 | 10/1970 | Sher | 128/742 |
| 3,592,060 | 7/1971 | Laverman | 374/43 |
| 3,688,558 | 9/1972 | Tixier | 374/45 |
| 3,798,003 | 3/1974 | Ensley et al. | 374/13 |
| 3,942,515 | 3/1976 | Servos et al. | 128/742 |
| 4,308,013 | 12/1981 | Major | 128/742 |

FOREIGN PATENT DOCUMENTS

| | | | |
|---|---|---|---|
| 2609415 | 9/1977 | Fed. Rep. of Germany | 128/742 |
| 2753109 | 6/1979 | Fed. Rep. of Germany | 128/742 |

OTHER PUBLICATIONS

George A. Gates MD et al. "The Thermoelectric Air Stimulator, a New Instrument for Vestibular Testing" *Arch Otolaryng*, vol. 92, Jul. 1970, pp. 80-84.
Bailey Instrument Company Product Literature.
H. Fruhstorfer et al. "Method for Quantitative Estimation of Thermal Thresholds in Patients," *J. Neurology, Neurosurgery and Psychiatry*, 1976,39, 1071-75.

*Primary Examiner*—Charles Frankfort
*Assistant Examiner*—W. Morris Worth
*Attorney, Agent, or Firm*—Charles J. Knuth; Peter C. Richardson; Mark Dryer

[57] ABSTRACT

A differential thermal testing system comprising a first thermal conductive sensing plate whose temperature is maintained at a constant first temperature, and a second thermal conductive sensing plate whose temperature can be altered. The temperature differential between the first thermal conductive sensing plate and second thermal conductive sensing plate is detected.

7 Claims, 3 Drawing Figures

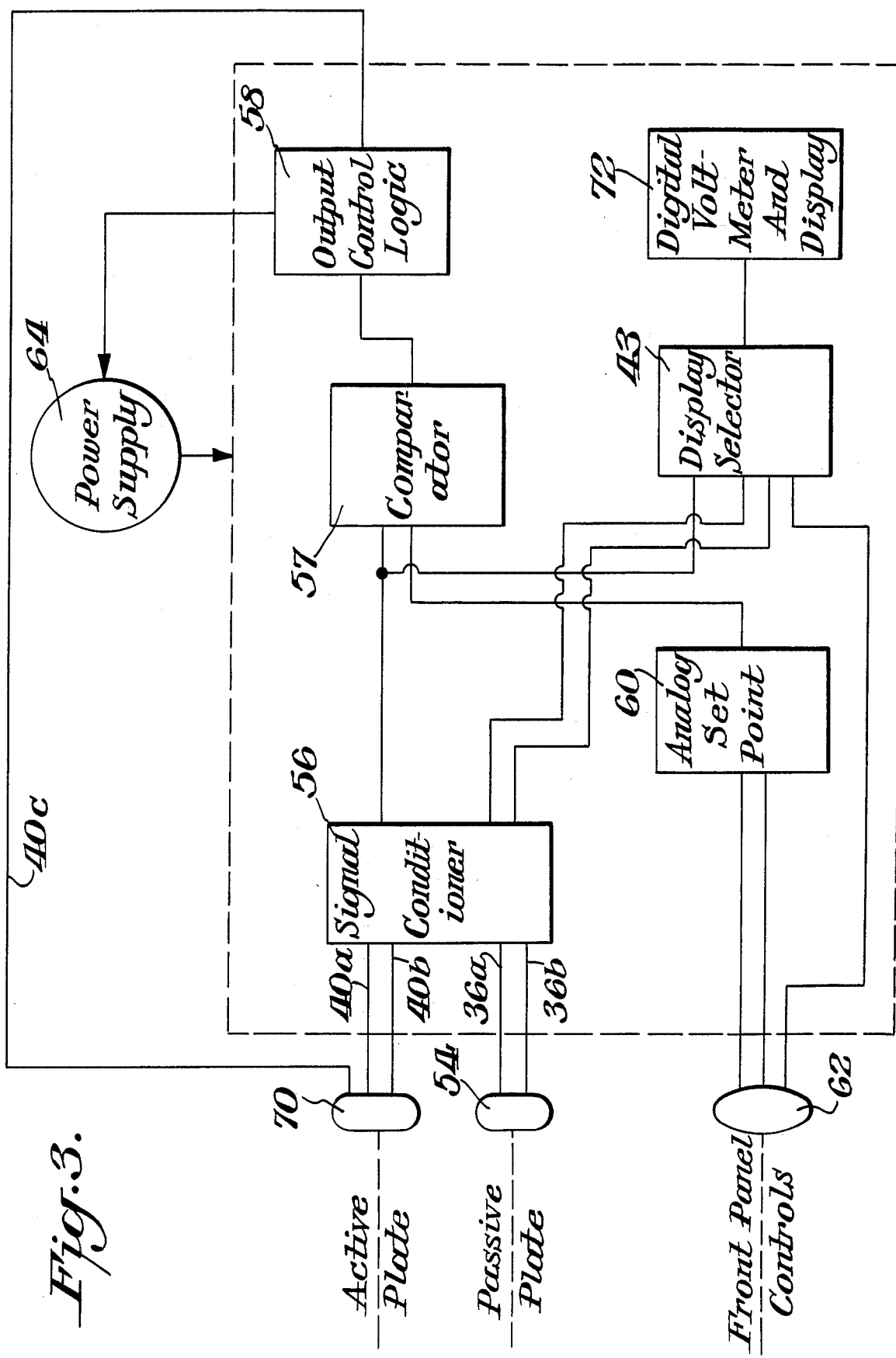

DIFFERENTIAL THERMAL TESTING APPARATUS AND METHOD

The present invention is directed to an apparatus and method for testing a subject for neuropathy. More particularly the present invention is directed to determining the ability of a subject to discriminate between two surfaces having different temperatures.

BACKGROUND OF THE INVENTION

Neuropathy is a general term used for diseases or lesions involving peripheral nerves. The present invention is directed to neuropathies which affect sensory nerve fibers. Neuropathy is a common problem, often causing weakness or pain, and is a complication which can accompany diabetes.

One method for determining neuropathy affecting sensory nerve fibers is described in Fruhstorfer et al., *Journal of Neurology, Neurosurgery, and Psychiatry*, 1976, 39, 1071–1075. The Marstock stimulator described therein was designed to provide a quantitative technique to measure warm, cold and thermal pain thresholds. With the Marstock method the area of the subject to be tested is kept on a surface whose temperature is raised or lowered until the subject perceives the surface temperature to be getting hotter or colder.

SUMMARY OF THE INVENTION

The present invention is directed to the discrimination of small differences in temperature rather than sensitivity to changes in temperature.

Embraced by the present invention is a differential thermal testing system comprising a first thermal conductive sensing plate, a second thermal conductive sensing plate, temperature altering means for altering the temperature of the second thermal conductive sensing plate, temperature maintaining means for maintaining the first thermal conductive means at a constant first temperature, and temperature detecting means for detecting the temperature differential between the first thermal conductive sensing plate and the second thermal conductive sensing plate.

Also included in the present invention is a method for determining the temperature sensitivity of an area of a subject comprising the steps of (a) contacting the area with a first thermal conductive sensing plate having a first temperature, (b) contacting the area with a second thermal conductive sensing plate having a second temperature, and (c) varying the temperature differential between the first thermal conductive sensing plate and the second thermal conductive sensing plate in order to determine the ability of the subject to discriminate between the first temperature and the second temperature.

BRIEF DESCRIPTION OF THE DRAWING

FIG. 3 is a block diagram showing the functional blocks and their use to control, sense and indicate temperature differences.

DETAILED DESCRIPTION OF THE INVENTION

Figure 1:
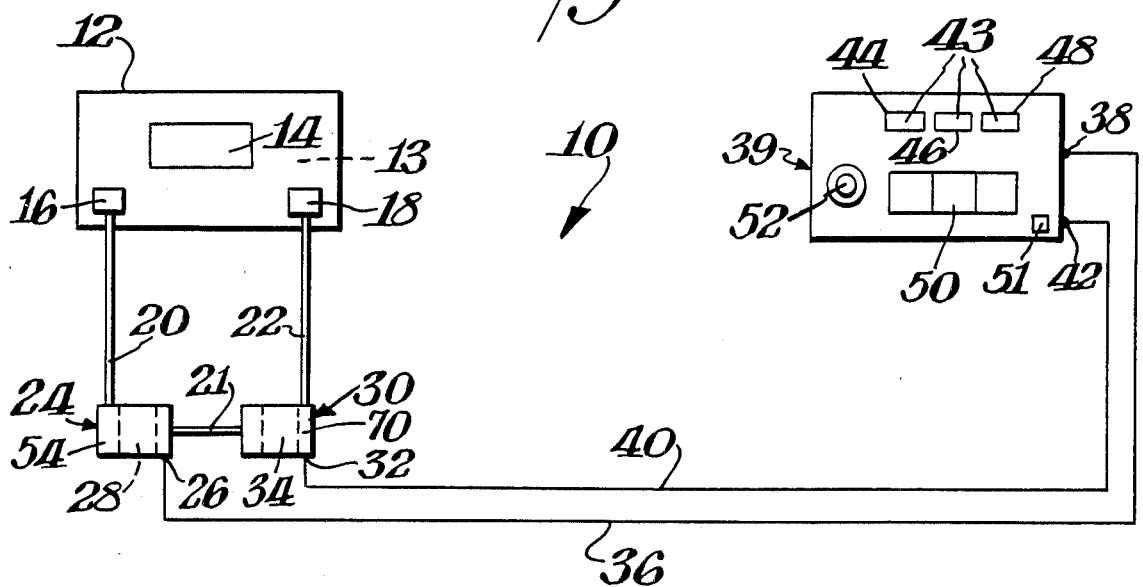
FIG. 1 is a schematic of a system of the present invention.

The present invention will be further illustrated by means of the Drawing. FIG. 1 is a schematic of a solid state closed loop bipolar temperature control system 10 of the present invention. The system 10 includes cooling unit 12, a first thermal conductive sensing device 24, a second thermal conductive sensing device 30, and a control and display unit 39.

The cooling unit 12 includes a coolant reservoir 13, a circulating fractional horsepower pump 14 having a coolant outlet 16 and a coolant reservoir return inlet 18. A suitable coolant is water although other coolants can be employed.

Figure 2:
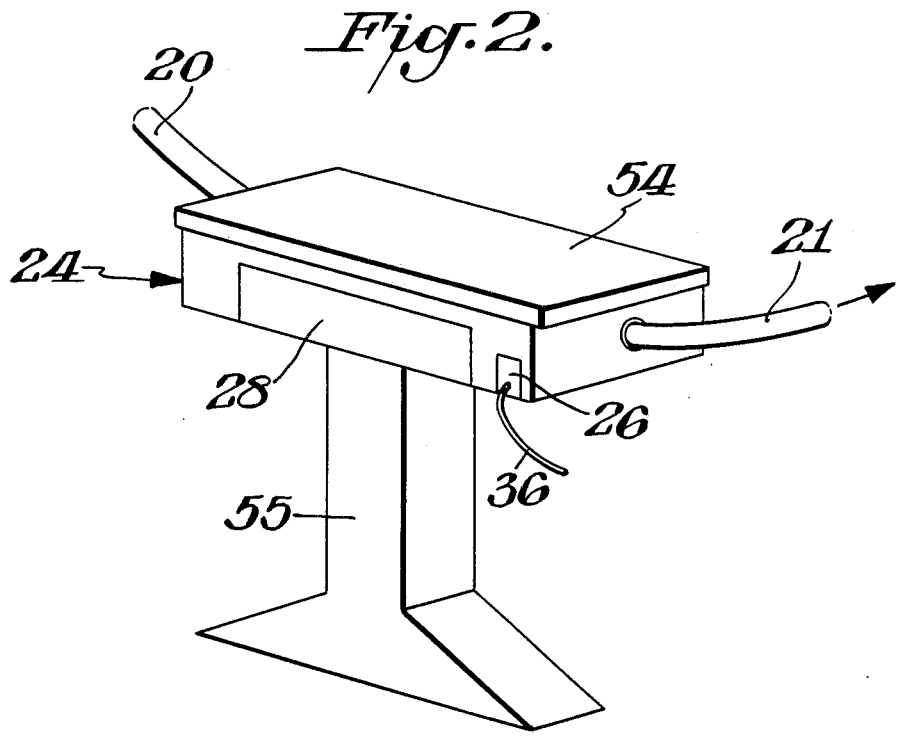
FIG. 2 is a perspective drawing of a thermal conductive sensing device.

A first coolant tube 20 connects the coolant outlet 16 to the first thermal conductive sensing device 24 which is shown in perspective view in FIG. 2. The first thermal conductive sensing device 24 and the second thermal conductive sensing device 30 have the same structure.

The first thermal conductive sensing device 24 has a first thermal conductive sensing plate 54 fabricated from a material having good thermal conductivity such as molybdenum or aluminum. The area of a subject whose temperature sensitivity is to be determined is placed on the top surface, having a convenient size such as $3 \times 4$ cm, of the first thermal conductive sensing plate 54. A first thermoelectric heat pump 28, which is a Peltier semiconductor device such as a Marlow Industries of Garland, Texas, single stage model MI 1120 having a heat capacity of 350 mwatts/°C., is connected by a first cable 36 to a first connector 38 and is bonded to the first thermal conductive sensing plate 54. The first cable can be, for example, Beldon part No. 83352 type E shielded Teflon electronic cable having two pairs of wires. The bonding can be accomplished by any convenient method which will lead to a good thermal coupling between the first thermal conductive sensing plate 54 and the first thermoelectric heat pump 28. For example, thermal epoxy can be employed for the bonding. The first thermal conductive sensing device 24 has a pedestal 55 for resting the device on a flat surface.

A first temperature sensing element 26, for example, a platinum resistance temperature device (rtd) available from Omego, Inc., Stamford, Conn., calibrated to DIN Standard 43760 (alpha=0.00385) is thermally bonded, for example, with a thermal epoxy, to the first thermal conductive sensing plate 54 and is connected with the first cable 36 which in turn is connected to the control and display unit 39 at the first connector 38. The temperature sensed by the first temperature sensing element 26 produces variations in its electrical output in accordance with a standard reference table such as DIN Standard 43760. These variations are transmitted by means of the first cable 36.

The second thermal conductive sensing device 30 has a second thermal conductive sensing plate 70 on which is placed the area of the subject for which the temperature sensitivity is to be determined, and a second thermoelectric heat pump 34, a second temperature sensing element 32 thermally bonded to the second thermal conductive sensing plate 70. A second cable 40 is connected to the control and display unit 39 at a second connector 42 and is also connected to the second temperature sensing element 32 and the second heat pump 34.

The thermoelectric heat pumps 28 and 34 in response to voltage polarity and amplitude have the ability to heat, cool or stabilize the temperature of the plate 54 or 70, respectively, being controlled.

A second coolant tube 21 connects the first thermal conductive sensing device 24 to the second thermal conductive sensing device 30. A third coolant tube 22 connects the second thermal conductive sensing device 30 to the coolant reservoir return inlet 18. The coolant tubes 20, 21 and 22 can be, for example, ¼ inch Tygon plastic tubing.

The control and display unit 39 includes an on/off switch 51, a display selector 43 having a first selector switch 44 which controls the display of the temperature of the second thermal conductive sensing plate 70, a second selector switch 46 which controls the display of the temperature of the first thermal conductive sensing plate 54, and a third selector switch 48 which controls the display of the differential temperature between the first thermal conductive sensing plate 54 and the second thermal conductive sensing plate 70.

A display 50 shows the information chosen by the display selector 43. The display 50 is preferably a three digit liquid crystal display although other display formats and alternate types of displays such as light emitting diodes may be employed.

The desired difference between the first thermal conductive sensing plate 54 and the second thermal conductive sensing plate 70 is set by means of a ten turn vernier dial control 52 capable of spanning 0.05° C. increments over a 0°-50° C. temperature range.

The system 10 is constructed so as to allow the temperature of the second plate 70 to be controlled to within 0.1° C. Such control is necessary in order to accurately and reproducably determine a subject's sensitivity to temperature differences and hence the extent of neuropathy in the test area of the subject.

The cooling unit 12 and tubes 20, 21 and 22 maintain the first thermal conductive sensing plate 54, called the passive plate, at a constant temperature, generally ambient room temperature, by pumping coolant through an internal chamber in the thermal conductive sensing plate 54. The coolant removes heat which the subject's area being tested adds to the passive plate 54. A recirculating coolant bath of sufficient volume to maintain the desired temperature of the passive plate 54 to within 0.1° C. will generally require about 1-3 gallons of coolant capacity and is commercially available.

The coolant flows in series through the second tube 21 to the second thermal conductive sensing plate 70, which is called the active plate and absorbs unwanted heat generated by the second thermoelectric heat pump 34. The coolant is then returned to the coolant reservoir 13, by means of the third tube 22 and the coolant reservoir return inlet 18. The volume of the coolant reservoir 13 allows the coolant to dissipate any heat so that ambient temperature is maintained. By having coolant pass through both the active and passive plates, 70 and 54, respectively, the subject will not choose a plate because it has more or less vibration than the other.

The control and display unit 39 obtains signals representative of the temperature of the plates 54 and 70, compares the actual difference between the plates 54 and 70 to the desired difference set by the dial control 52 and outputs the voltage necessary to maintain the desired differential by controlling the temperature of the active plate 70 by means of the second thermoelectric heat pump 34.

FIG. 3 is a block diagram showing the functional blocks and their use to control, sense and indicate the temperature difference between the active plate 70 and the passive plate 54.

The signal conditioner 56, for example, one employing two precision instrumentation amplifiers such as the Analog Devices AD521 and associated passive components, amplifies and scales the voltage produced by the sensing elements 26 and 32 and outputs an analog voltage equivalent to the temperature in °C. of each plate 54 and 70 for use by a comparator 57 and the display selector 43.

The display selector routes the active plate 70, passive plate 54 or differential temperature signal to a digital voltmeter and display 72. The voltmeter can be, for example, Simpson digital panel meter series 2865 DPM. The signal represents a temperature in °C. which is shown on the display 50.

The selector dial 52 enables the operator to set the desired difference in temperature between the active plate 70 and passive plate 54. This setting is converted to an analog set point 60 which is an analog voltage output equal to the desired temperature difference between the plate 54 and 70 temperatures.

The comparator 57, for example, a National Semiconductor LM311 voltage comparator, compares the difference voltage from the signal conditioner 56 and the analog set point voltage 60. The resultant of the comparison is sent to the output control logic 58, which is a complementary power transistor amplifier/drive, as an error signal.

The error signal is processed by the output control logic 58 and a signal is generated which causes the active plate 70 temperature to increase or decrease, as appropriate, until the actual temperature difference between the active plate 70 and the passive plate 54 is equal to the desired difference set at the selector dial 52. The system 10 is a closed loop system which continuously compares the actual temperature differential with the desired temperature differential and modifies the bipolar output to maintain the required temperature differential.

A power supply 64 provides regulated voltages necessary for the logic elements incorporated in FIG. 3 and the necessary power for the thermoelectric pumps 34 and 28.

A two wire pair consisting of 40a and 40b of the second cable 40 is connected to the signal conditioner 56 from the active plate 70. A remaining pair in 40c are connected to the output control logic 58 from the active plate 70.

A two wire set 36a and 36b of the first cable 36 is connected from the passive plate 54 to the signal conditioner 56. No connection is made between the passive plate 54 and the output control logic 58 since the temperature of the passive plate is maintained by means of the coolant flow.

Commercially available equipment can be modified to obtain a system of the present invention. For example, a Bailey Instrument Co., Saddle Brook, N.J., Model BFS-2TC Temperature Controlled Cold/Hot Plate complete with a Unit/Power Supply can be altered by adding resistors to the voltage control mechanism of the thermal control unit to reduce the temperature range of the active plate to between about 0° and 50° C. The Bailey equipment's normal operating range of −40° to +60° C. can lead to tissue damage if improperly set. Also, a fine control knob, calibrated in 12 fixed steps of 0.1° C. is preferably added to the voltage control. This knob is used in conjunction with the coarse temperature setting control in the final stages of testing and greatly reduces the time required to achieve specific temperature settings. The BFS-2TC includes a 3×4 cm. Peltier thermal conductive sensing device.

The system of the present invention also includes a second 3×4 cm. Peltier thermal conductive sensing device for the BFS-2TC, a TH-6D display differential thermometer, a connector cable for connecting the BFS-2TC to the display differential thermometer, two stage mountings, and one PT-6 package of probes, all available from Bailey Instrument Company. Cable connects each temperature sensing device to the display thermometer. The active plate Peltier device is connected to the controller and the temperature sensing device of the active plate is also connected to the controller. The two plates, one active and one passive, are perfused in series with water as previously described.

The device of the present invention is adapted to quantify the ability of human subjects to detect small changes in temperature, particularly at the distal extremes of their upper and lower limbs. As a result, the device and testing methodology can be employed to monitor the integrity of small diameter neurons when a drug which may be useful for treating diabetes complications is being tested.

Prior to testing, all subjects should be provided with an adaptation period of between 10 or 15 minutes during which they can become accommodated to room temperature. At the end of this period, the surface temperature of the subject's skin at the site to be tested, should be determined, preferably to the nearest 0.1° C. Skin temperature can be measured using the digital thermometer in a direct mode. The thermal sensor probe can plug into either the active or passive section of the thermometer.

Following the adaptation period, each subject should be given an opportunity to become familiar with the testing apparatus and with the expected thermal sensations. A number of temperatures should be set and sampled by the subject. During this period, the experimenter can instruct the subject as to the appropriate time and pressure with which to touch the plates. At the beginning of the test period, the following instructions, for example, may be issued:

"Please press your finger against each plate in turn. Press firmly and for approximately one second at the center of each plate. One of the two plates will feel cooler and you must decide if it is the right or left plate. The plates will never be the same temperature and you must make a decision on each trial. The task will become progressively more difficult, so please do not get discouraged. I understand that you will be apparently guessing on many of the trials."

For the initial trial, the experimenter should set the temperature differential at a level that is detectable 100% of the time. For many subjects in the 20 to 70 year range, an initial temperature differential of 5.0° C. is sufficient. This level should be increased for subjects with suspected neuropathy, for older subjects, or when testing the feet. An estimate of the appropriate initial level for an individual subject can be determined during the pre-test period. The sign (±) of the digital readout will inform the experimenter whether the active or passive plate is actually cooler. The instrument setting, the subject's choice and whether correct or incorrect can be recorded.

If the subject is correct, the temperature differential used in the initial test may be reduced by approximately 10% for the next trial and this process may be continued until the first error. This percentage is not an exact requirement, but rather a guideline. If the temperature differential falls below 1.0° C., all changes may be made in 0.1° C. steps using the fine control knob. When the subject makes his/her first error, the identical temperature should be repeated on three successive trials. If the correct position is selected on two of the three trials, the temperature is lowered. If errors are made on two of the three trials, the temperature should be raised. All levels below 0.7° C. should be repeated twice—even if the subject selects the correct position.

Testing is completed when the subject has made a total of three errors. At this time, the surface temperature of the passive plate (direct reading on the digital thermometer) should be entered on the data sheet. Throughout testing, the location of the cooler surface must be randomized across both the active and passive plates. A two-choice randomization table may be helpful in selecting the testing sequence.

For accurate thermal testing, the experimenter should be concerned with the following details:

1. The subject should be consistent in the location of touch and the approximate force applied to each plate. Instructions such as "please press more firmly" can be issued during testing to insure trial to trial consistency.

2. The time interval between trials is preferably standardized at approximately 15 seconds. It physically takes longer to set a new temperature level that requires crossing the zero point (i.e. $-2.6$ to $+2.3$) as compared with the one on the same side of the zero point (i.e. $-2.6$ to $-2.3$). This factor must not be reflected in the time period between trials since it can provide a nonthermal clue.

3. When testing at the same level as the previous trial, the sounds and motions associated with temperature change should be simulated by the experimenter.

4. The subject should be carefully screened from viewing the instrument setting or the data sheet.

The procedures for determining thermal threshold on the feet are identical to those described above, with the large toe on one foot being brought into contact with the plate. This can be facilitated by positioning the plate on the floor or on a slightly elevated platform (approximately 6"). If the subject experiences difficulty in making consistent contact with the stimulating surface, the experimenter should guide the toe to the appropriate target. In extreme cases, the plate may be disconnected from the support platforms, and manually held against the toe in sequence. The manual positioning of the plates can be used to test threshold in the more proximal portions of either the upper or lower limb.

Absolute threshold—The first step in calculating the absolute threshold of detectable temperature differential is to determine the temperature differential values of the three errors and the three lowest correct scores. The highest and lowest values of these six scores are eliminated and the mean of the remaining four scores determines the absolute thermal threshold. This procedure is designed to utilize a sufficient sample of data points and to eliminate a disproportionate contribution of a single anomalous score to the absolute threshold. Another preferred method is to employ the temperature values of five errors and the five lowest correct scores, eliminate the highest and lowest value and determine the mean of the remaining eight scores to determine the absolute thermal threshold.

Relative threshold—A second value that can be obtained for each subject is the calculated absolute threshold expressed as a percentage of the temperature of the passive plate. Thus, an absolute threshold of 0.6° C.

would translate to a relative threshold of 2.4% if the passive plate had a reading of 25° C. and to a value of 3.0% if the passive plate was at 20° C. Over the mid-range of stimulus intensity, it has been demonstrated in the somatosensory, auditory, and visual modalities that the minimal detectable change in energy is approximately proportional to the total energy of the comparison stimulus. This is expressed as Weber's law ($\Delta 1/1 = C$) where 1 equals stimulus intensity and C is a constant that differs for each modality. Expressing thermal sensitivity as a relative threshold would be of great value in circumstances where the temperature of the passive plate could be expected to differ by a significant amount between test periods. An alternative to expressing threshold values as a percentage is to correct the absolute threshold score by a factor reflecting differences in the passive plate. In this manner temperature could continue to be expressed in degrees centigrade.

Thirty-nine subjects were tested with the procedures outlined above and their thresholds for finger stimulation were determined. The subjects ranged in age from 16 to 88 and all were free of any history of neurological deficit. The mean absolute threshold for this population was 0.65° C., and the standard deviation was 0.20° C. It was not necessary to calculate relative threshold as the temperature of the passive plate did not vary by more than 2.5° C. over the testing period. There is an apparent decline in thermal sensitivity and an increase in variance as a function of age. The thresholds for male and female did not significantly differ at the 0.05 level.

Thermal absolute thresholds were obtained in eight subjects for stimulation of the toes, with a mean of 0.88° C. Many subjects had thresholds which were approximately equivalent for fingers and toes.

I claim:

1. A differential thermal testing system for determining the temperature sensitivity of an area of a subject comprising:
   a reservoir for holding liquid coolant;
   a first thermal conductive sensing device comprising, in combination, a first thermal conductive sensing plate having an exposed surface adapted to be placed in contact with said area of a subject, a first thermoelectric heat pump thermally coupled to said first sensing plate and adapted to heat, cool or stabilize the temperature of said plate, a first temperature sensing element associated with said first sensing plate and having a first electronic cable connection to a control and display unit;
   a first coolant tube for conveying liquid coolant from said reservoir to said first sensing device and maintaining said first sensing plate at a constant first temperature;
   a second thermal conductive sensing device comprising, in combination, a second thermal conductive sensing plate having an exposed surface adapted to be placed in contact with said area of a subject, a second thermoelectric heat pump thermally coupled to said second sensing plate and adapted to heat, cool or stabilize the temperature of said plate, a second temperature sensing element associated with said second sensing plate and having a second electronic cable connection to said control and display unit;
   a second coolant tube connecting said first sensing device to said second sensing device and a third coolant tube connecting said second sensing device to said reservoir, so that the series of coolant tubes, sensing devices and reservoir form a closed circuit of circulating liquid coolant;
   said control and display unit being adapted to receive and transmit signals from said first and second sensing devices and thereby controlling the output of the respective thermoelectric heat pumps to establish a temperature differential between said constant temperature of said first sensing plate and an altering temperature of said second sensing plate and detecting and displaying said temperature differential.

2. A system according to claim 1 wherein each of said first and second thermoelectric heat pump includes a Peltier effect semiconductor device.

3. A system according to claim 1 wherein the first temperature is ambient room temperature.

4. A method for determining the temperature sensitivity of an area of a subject using,
   a differential thermal testing system for determining the temperature sensitivity of an area of a subject comprising:
   a reservoir for holding liquid coolant;
   a first thermal conductive sensing device comprising, in combination, a first thermal conductive sensing plate having an exposed surface adapted to be placed in contact with said area of a subject, a first thermoelectric heat pump thermally coupled to said first sensing plate and adapted to heat, cool or stabilize the temperature of said plate, a first temperature sensing element associated with said first sensing plate and having a first electronic cable connection to a control and display unit;
   a first coolant tube for conveying liquid coolant from said reservoir to said first sensing device and maintaining said first sensing plate at a constant first temperature;
   a second thermal conductive sensing device comprising, in combination, a second thermal conductive sensing plate having an exposed surface adapted to be placed in contact with said area of a subject, a second thermoelectric heat pump thermally coupled to said second sensing plate and adapted to heat, cool or stabilize the temperature of said plate, a second tepmerature sensing element associated with said second sensing plate and having a second electronic cable connection to said control and display unit;
   a second coolant tube connecting said first sensing device to said second sensing device and a third tube connecting said second sensing device to said reservoir, so that the series of coolant tubes, sensing devices and reservoir form a closed circuit of circulating liquid coolant;
   said control and display unit being adapted to receive and transmit signals from said first and second sensing devices and thereby controlling the output of the respective thermoelectric heat pumps to establish a temperature differential between said constant temperature of said first sensing plate and an altering temperature of said second sensing plate and detecting and displaying said temperature differential comprising the steps of:
   (a) contacting the area with said first thermal conductive sensing plate having a first temperature;
   (b) removing the area from the first thermal conductive sensing plate and contacting the area with said second thermal conductive sensing plate having a second temperature; and (c) varying the temperature differential between the first thermal conductive sensing plate and the second thermal conductive sensing plate in order to determine the ability of the subject to discriminate between the first temperature and the second temperature.

5. A method according to claim 4 wherein the first thermal conductive sensing plate is a passive plate and the second thermal conductive sensing plate is an active plate.

6. A method according to claim 4 wherein step (c) comprises altering the temperature of the second thermal conductive sensing plate.

7. A method according to claim 6 wherein the temperature is altered by means of a Peltier effect semiconductor device.

* * * * *